(12) United States Patent
Davis et al.

(10) Patent No.: US 12,605,504 B2
(45) Date of Patent: Apr. 21, 2026

(54) HIGH ACCURACY CLAMP ASSEMBLY

(71) Applicant: CareFusion 303, Inc., San Diego, CA (US)

(72) Inventors: Lisa M. Davis, San Antonio, TX (US); Jarod Dias, San Diego, CA (US)

(73) Assignee: CAREFUSION 303, INC., San Diego, CA (US)

( * ) Notice: Subject to any disclaimer, the term of this patent is extended or adjusted under 35 U.S.C. 154(b) by 0 days.

(21) Appl. No.: 18/810,243

(22) Filed: Aug. 20, 2024

(65) Prior Publication Data

US 2026/0054008 A1 Feb. 26, 2026

(51) Int. Cl.
*A61M 5/168* (2006.01)

(52) U.S. Cl.
CPC .... *A61M 5/16813* (2013.01); *A61M 5/16881* (2013.01); *A61M 2205/3334* (2013.01)

(58) Field of Classification Search
CPC .......... A61M 5/16813; A61M 5/16881; A61M 2205/3334
USPC ............................................................. 251/6
See application file for complete search history.

(56) References Cited

U.S. PATENT DOCUMENTS

| | | | | | |
|---|---|---|---|---|---|
| 4,065,093 | A | * | 12/1977 | Phillips | A61M 39/286 251/6 |
| 4,265,425 | A | | 5/1981 | Morin | |
| 4,335,866 | A | * | 6/1982 | Bujan | A61M 39/286 251/9 |
| 4,406,440 | A | * | 9/1983 | Kulle | A61M 39/286 251/6 |
| 4,911,399 | A | * | 3/1990 | Green | A61M 39/285 251/6 |
| 5,318,546 | A | * | 6/1994 | Bierman | A61M 1/83 251/6 |
| 5,721,024 | A | * | 2/1998 | Carmen | A61J 1/10 604/408 |
| 6,129,330 | A | * | 10/2000 | Guala | A61M 39/286 251/6 |
| 6,536,739 | B1 | * | 3/2003 | Jensen | F16K 7/065 251/6 |
| 6,929,236 | B1 | * | 8/2005 | Height | A61M 39/286 137/553 |

(Continued)

OTHER PUBLICATIONS

International Search Report and Written Opinion for Application No. PCT/US2025/042080, dated Dec. 2, 2025, 14 pages.

*Primary Examiner* — Patrick C Williams
(74) *Attorney, Agent, or Firm* — MASCHOFF BRENNAN

(57) ABSTRACT

A clamp assembly for adjusting the fluid flow rate in an infusion set is provided. The clamp assembly includes a housing having two opposing side walls spaced apart from each other and having opposing guide grooves, a guide wall disposed between the side walls, an elastomeric segment disposed between the two opposing side walls and the guide wall, the elastomeric segment having a lower compression set performance that the compression set performance of first and second IV tubes of the infusion set, and first and second tubing ports. A flow-regulating member is seated in the guide grooves and is configured to remain in a set position during use of the infusion set based on the compression set performance of the elastomeric segment until the roller wheel is moved by a user. A method of operating a clamp assembly is also provided.

8 Claims, 5 Drawing Sheets

(56) References Cited

U.S. PATENT DOCUMENTS

| | | | |
|---|---|---|---|
| 8,568,370 B2 * | 10/2013 | Chew ................ | A61M 5/16881 |
| | | | 604/249 |
| 2019/0381223 A1 * | 12/2019 | Culbert ................. | A61M 1/772 |

* cited by examiner

400

410

Couple tubing to clamp assembly

420

Move flow-regulating member to reach
first clinical flow rate

430

Move flow-regulating member to reach
second clinical flow rate

440

Move flow-regulating member to reach
third clinical flow rate

HIGH ACCURACY CLAMP ASSEMBLY

CROSS REFERENCE TO RELATED APPLICATION

None

TECHNICAL FIELD

The present disclosure generally relates to a gravity intravenous (IV) set or infusion pump flow control device, and in particular a high accuracy clamp assembly for IV administration.

BACKGROUND

Infusion sets allow for the administration of medication and infusates from a container to the patient via an IV Line, which enters the patient through a needle/catheter. The control of the fluid flow into the patient is done by gravity or through the use of an IV pump. The control of gravity flow through an IV set is most often accomplished through a roller clamp that consists of a housing with a ramped track through which the IV tubing passes. A wheel that travels along the angled track allows full flow in the open position and when moved across the track applies increasing compression force to the external surface of the tubing minimizing the cross-sectional area of the flow path, thus slowing flow rate down. Once the wheel reaches the end of the track the internal fluid path is completely occluded, stopping infusate flow.

Historically these roller clamps have a problem with flow rate drift. As the flow rate is set by compressive forces, the flexible tubing alters its shape and continues to creep over time. In turn, this causes the flow rate to change if the roller clamp is left in the same position for an extended period.

Thus, it is desirable to provide a high accuracy clamp assembly that alters the form of the typical roller clamp in such a way as to provide better accuracy over time when the clinician sets the clamp to the desired flow rate. It is also desirable to maintain common identifying features of typical roller clamps so that this standard component does not become unrecognizable to the end user and does not significantly alter common flow control practice.

SUMMARY

One or more embodiments provide a clamp assembly comprising: a housing configured to couple to an infusion set, the housing comprising: two opposing side walls spaced apart from each other, each side wall having an opposing guide groove longitudinally positioned in an interior surface; a guide wall disposed between the side walls; an elastomeric segment disposed between the two opposing side walls and the guide wall, the elastomeric segment having a lower compression set performance that the compression set performance of first and second IV tubes of the infusion set; a first tubing port disposed on a first end of the elastomeric segment and configured to couple with the first IV tube of the infusion set; and a second tubing port disposed on a second end of the elastomeric segment and configured to couple with the second IV tube of the infusion set; and a roller wheel having two axial projections slidingly seated in the guide grooves, the roller configured to move along a longitudinal axis of the housing over a movement range as the projections slide in the guide grooves, wherein the roller wheel is configured to remain in a set position during use of the infusion set based on the compression set performance of the elastomeric segment until the roller wheel is moved by a user.

One or more embodiments provide a clamp assembly comprising: a housing configured to couple to an infusion set, the housing comprising: two opposing side walls spaced apart from each other, each side wall having an opposing guide track longitudinally positioned in an interior surface; a guide wall disposed between the side walls; an elastomeric membrane disposed on the guide wall between the two opposing side walls, the elastomeric membrane having a lower compression set performance that the compression set performance of first and second IV tubes of the infusion set; a first tubing port disposed on a first end of the elastomeric membrane and configured to couple with the first IV tube of the infusion set; and a second tubing port disposed on a second end of the elastomeric membrane and configured to couple with the second IV tube of the infusion set; and a flow-regulating member having two portions slidingly seated in the guide tracks, the flow-regulating member configured to move along a longitudinal axis of the housing over a movement range as the two portions slide in the guide tracks, wherein the flow-regulating member is configured to remain in a set position during use of the infusion set based on the compression set performance of the elastomeric membrane until the flow-regulating member is moved by a user.

One or more embodiments provide a method of operating a clamp assembly. The method includes inserting a first intravenous (IV) tube of an infusion set into a first tubing port of a high accuracy clamp assembly; inserting a second IV tube of the infusion set into a second tubing port of the high accuracy clamp assembly, the high accuracy clamp assembly comprising a housing having two opposing side walls spaced apart from each other, each side wall having an opposing guide groove longitudinally positioned in an interior surface, a guide wall disposed between the side walls, an elastomeric membrane disposed on the guide wall between the two opposing side walls and between the first and second tubing ports, and a flow-regulating member slidingly seated in the guide grooves; moving the flow-regulating member to a first position along the guide groove to engage the elastomeric membrane, causing a flow rate of fluid through the elastomeric membrane to go from a fully open flow rate to a first controlled clinical flow rate; and maintaining the flow-regulating member in the first position during use of the infusion set until the flow-regulating member is moved again by a user based on a compression set performance of the elastomeric membrane being lower than the compression set performance of the first and second IV tubes of the infusion set.

The foregoing and other features, aspects and advantages of the disclosed embodiments will become more apparent from the following detailed description and accompanying drawings.

BRIEF DESCRIPTION OF THE DRAWINGS

The accompanying drawings, which are included to provide further understanding of the disclosure and are incorporated in and constitute a part of this specification, illustrate embodiments of the disclosure and together with the description serve to explain the principles of the disclosure.

DETAILED DESCRIPTION

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions are provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

Figure 1:
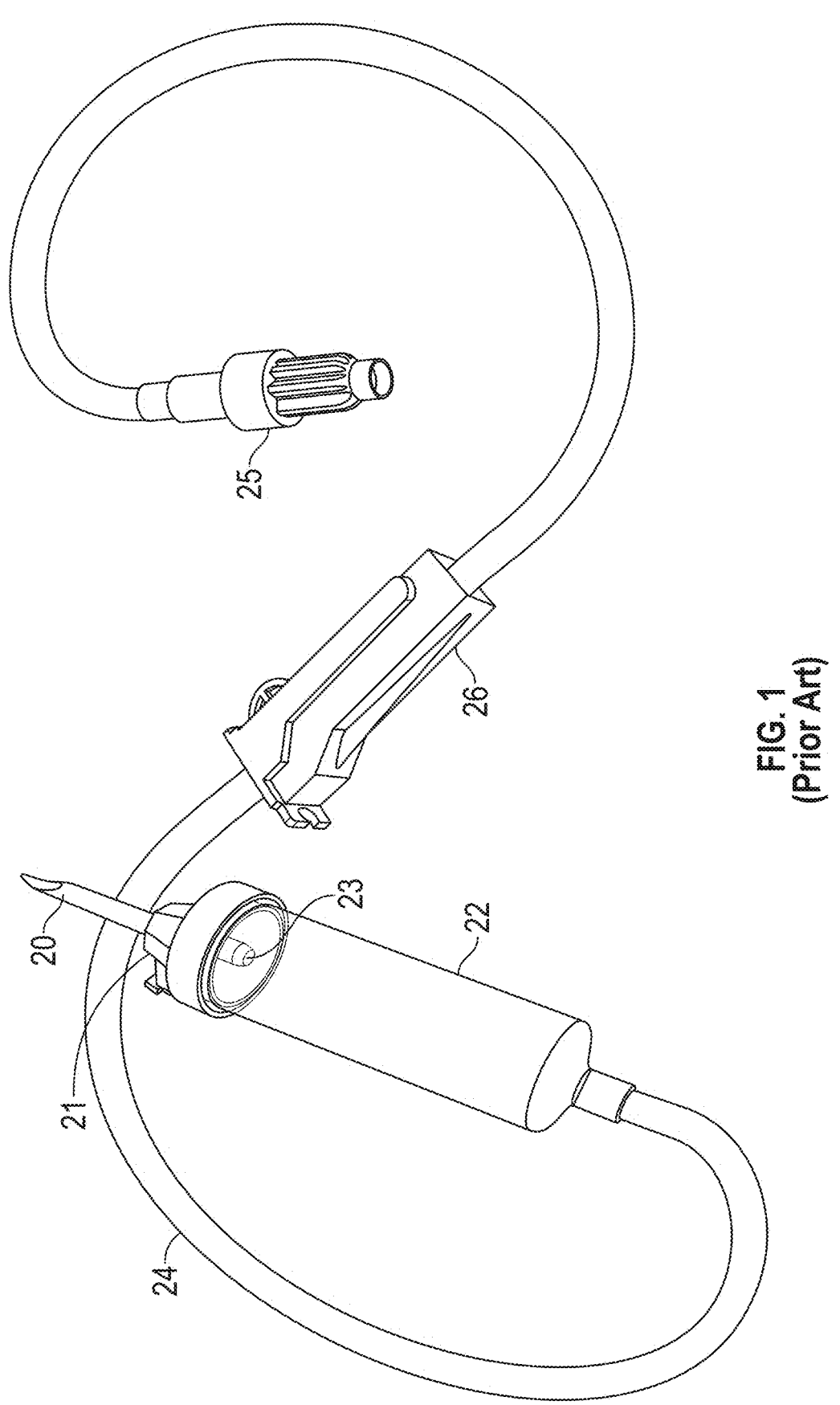
FIG. 1 depicts a perspective view of an example infusion set having a typical roller clamp.

The present disclosure relates to a roller clamp and in particular to a roller clamp for use in gravity administration sets, pump sets, secondary sets, or any other sets that may use a roller clamp to regulate the flow of an infusion. The roller clamp regulates the flow rate of a medical fluid (for example a solution of a drug to be administered to a patient, or blood) flowing through a tube. Typically, a standard infusion set is used to infuse the fluid. An example of a standard infusion set is shown in FIG. 1.

The infusion set includes a piercing spike 20 which may either be a sharp spike for piercing rubber stoppers or rounded and blunt for insertion into a bag. The spike contains one channel for fluid and optionally a second channel for venting. A vent 21 is usually present in the vicinity of the piercing spike to allow air to flow into the drop chamber 22. The vent 21 may be provided with a bacterial filter to prevent bacteria from entering the equipment.

The drop chamber 22 has a drop generator 23 at the top of the drop chamber 22 that produces drops of a certain size. Drops from the drop generator 23 fall into the drop chamber 22 such that the drop chamber 22 is partially filled with fluid or liquid. This prevents air bubbles from entering the connector tube 24, which would be harmful to a patient. A particle filter may be provided at the lower aperture of the drop chamber 22.

The connector tube 24 connects the drop chamber 22 with the patient. The connector tube 24 is usually a minimum of 150 cm long and can be manufactured from Polyvinyl Chloride (PVC). The tube 24 is shown shortened in FIG. 1 for clarity. The connector tube 24 typically has a continuous diameter throughout the length of the tube.

At the end of the connector tube 24 is a Luer fitting 25 which is standardized for connection to all other pieces of apparatus having a standard Luer cone. The person skilled in the art will appreciate that the Luer fitting 25 can be fitted to a hypodermic needle (not shown) for infusing the medical fluid into the circulatory system of a patient (e.g., into a vein).

Between the drop chamber 22 and the Luer fitting 25 and engaging with the connector tube 24, is a roller clamp 26. The present disclosure is concerned with an improved roller clamp assembly, but a typical roller clamp 26 as known in the art will now be described for background information.

Figure 2:
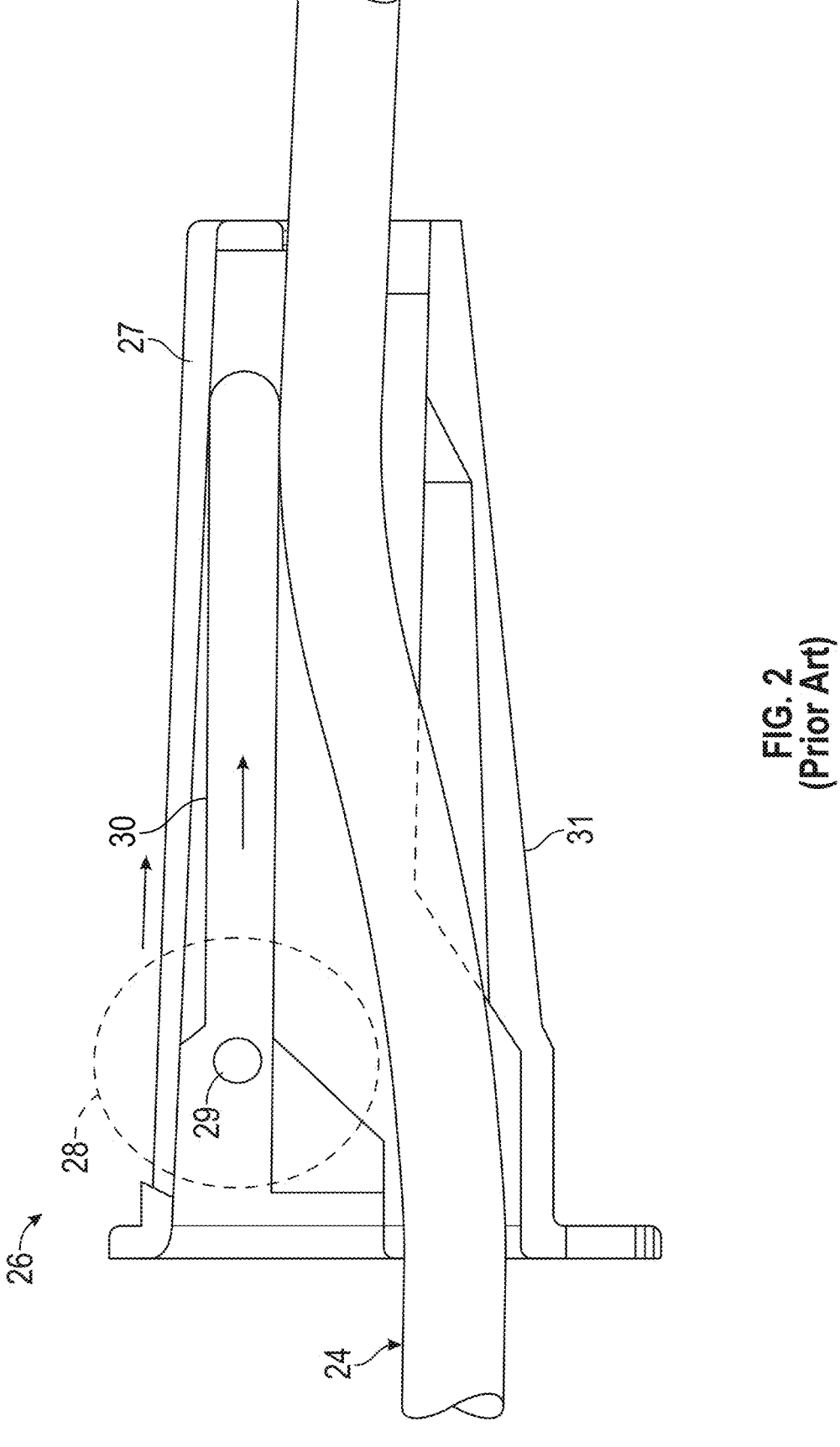
FIG. 2 depicts a cross-section side view of the roller clamp of FIG. 1.

The roller clamp 26 illustrated in FIG. 2 has a housing 32 with two opposing side walls 27 having a pair of guide grooves 30 that are aligned with each other and face each other. A flow-regulating roller wheel 28 is provided having axially-projecting shafts 29 protruding from the centers of each side of the roller wheel 28. The roller wheel 28 is shown in outline for clarity. The shafts 29 of the roller 28 are captured by and seated in the guide grooves 30 so that the roller wheel 28 can move up and down the guide grooves 30 along the housing 32 as indicated by the arrows in FIG. 2.

The entire roller clamp 26 has four walls (see FIG. 1) in an open-ended boxlike construction and is dimensioned and configured to receive the connector tube 24. In use, the tube 24 passes through the roller clamp 26, between the two opposing side walls 27, the roller wheel 28 and a guide wall 31 that is opposed to the roller wheel 28.

In the roller clamp 26, the surface of the guide wall 31 converges along its length toward the position of the guide grooves 30 in the downward direction of the guide grooves 30 (e.g., in the direction of the arrows in FIG. 2). This tends to urge the connector tube 24 within the roller clamp 26 toward the guide grooves 30 and thus toward roller wheel 28.

Thus, rolling the roller wheel 28 downwardly along the guide grooves 30 in the direction of the gradually closer guide wall 31 in the direction of the arrows causes the roller wheel 28 to impinge against the connector tube 24. As the roller wheel 28 impinges on the tube 24, the tube 24 becomes squeezed, as it is a flexible material such as PVC, and the lumen of the infusion tube 24 therefore becomes smaller. In this way, by narrowing of the lumen, the flow rate of fluid passing through the connector tube 24 can be regulated.

Thus, the roller clamp 26 controls the flow rate through the infusion tube 24 by clamping the infusion tube 24 between the roller wheel 28 and the guide wall 31. As discussed above, this provides for a course flow rate change because a small movement of the roller wheel 28 causes a large change in the flow rate of the fluid through the tube 24. Also, the force of the fluid in the tube 24 exerts a biasing force against the roller wheel 28, which often leads to slippage of the wheel roller 28 (e.g., the roller wheel 28 rolls back) from the adjusted position.

As discussed above, current roller clamps experience flow rate drift wherein as the flow rate is set by compressive forces, the flexible tubing alters its shape and continues to creep over time and cause the flow rate to unintentionally change, particularly if the roller clamp is left in the same position for an extended period.

IV tubing is typically constructed from plasticized PVC. This material, when held statically in a compressed state, allows for creep to take place. Consequently, the clinician may set a typical roller clamp to a delivery rate of 125 ml/hr and return to the patient finding that the IV tubing has yielded under the pressure of the wheel and the flow rate has decreased substantially, for example. Often times the clinician must massage the tubing to become round again and reset the rate or move the clamp to another position on the IV tubing and reset the rate. In the meantime, the delivery of the medication to the patient is delayed and the same rate may not accurately be obtained again.

In aspects of the disclosure, a high accuracy clamp assembly provides improved accuracy via the implementation of an elastomeric feature which allows the clinician to set the desired flow rate and come back later to find that the flow rate is not substantially changed, unlike as is the case with the standard roller clamp configuration.

In aspects of the disclosure, a solution to the compression issues of PVC tubing is to use an elastomeric feature instead. In aspects of the disclosure, the elastomeric feature may be tubing extruded from a material with reduced compression set performance such as silicone rubber, Thermoplastic Polyurethane (TPU), Thermoplastic Elastomer (TPE) or ultra-high molecular weight (UHMW) PVC.

In aspects of the disclosure, a housing with an over-molded elastomeric material may be used that can be compressed by a wheel, a gear, or a lubricated protrusion from a sliding feature or a sliding feature guiding a glass ball up and down the track of the clamp housing.

In aspects of the disclosure, the high accuracy clamp assembly is similar enough to a typical roller clamp so that the clinician will easily recognize the component's function as well as ensuring that basic flow control practice is not altered for the end user.

Figure 3:
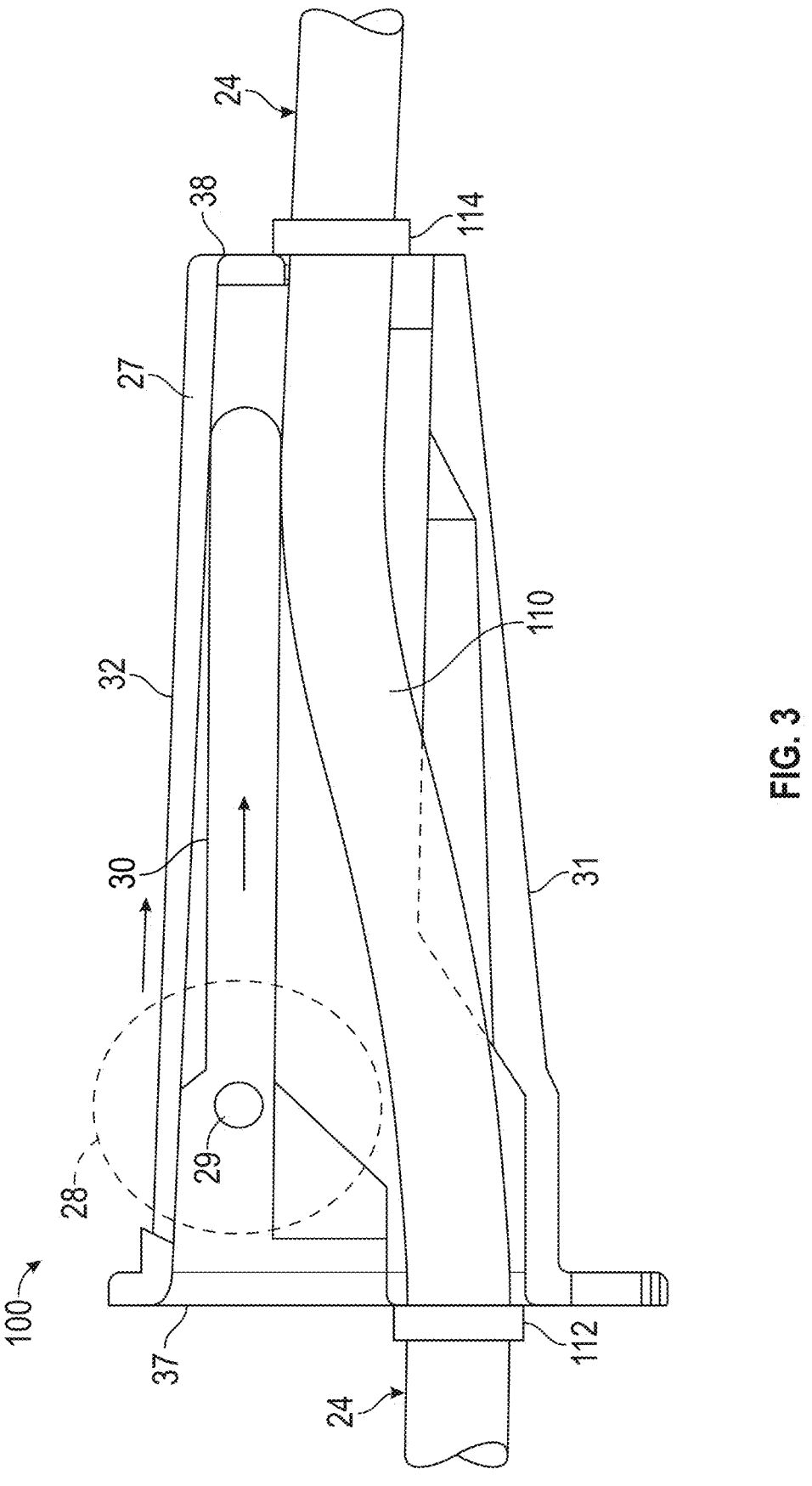
FIG. 3 depicts a cross-section side view of a high accuracy clamp assembly, according to aspects of the disclosure.

With reference to FIG. 3, a high accuracy clamp assembly 100 is shown. The high accuracy clamp assembly 100 may have most of the features of roller clamp 26. For example, high accuracy clamp 100 illustrated in FIG. 3 has a housing 32 with two opposing side walls 27 having a pair of guide grooves 30 that are aligned with each other and face each other. A flow-regulating member 128 (e.g., roller wheel 28) is provided having axially-projecting shafts 29 protruding from the centers of each side of the flow-regulating member 128, which is shown in outline for clarity. The shafts 29 of the flow-regulating member 128 are captured by and seated in the guide grooves 30 so that the flow-regulating member 128 can move up and down the guide grooves 30 along the housing 32 as indicated by the arrows in FIG. 3 (e.g., from first housing end 37 towards second housing end 38).

However, instead of receiving standard PVC IV tubing (e.g., IV tube 24) within the housing 32 as is done in roller clamp 26, the high accuracy clamp assembly 100 further includes an elastomeric segment 110 disposed within the housing 32. The elastomeric segment 110 is disposed between the two opposing side walls 27, the flow-regulating member 128 and a guide wall 31 that is opposed to the flow-regulating member 128. The elastomeric segment 110 may be formed of an elastomeric material such as silicone rubber, TPE, TPU or UHMW PVC, for example. The elastomeric segment 110 includes a tubing port 112 on the first housing end 37 and a tubing port 114 on the second housing end 38. Here, each of the tubing ports 112, 114 is configured to sealingly couple with an end of an IV tube 24 (e.g., PVC tubing).

In use, rolling the flow-regulating member 128 downwardly along the guide grooves 30 in the direction of the gradually closer guide wall 31 in the direction of the arrows causes the flow-regulating member 128 to impinge against the elastomeric segment 110. As the flow-regulating member 128 impinges on the elastomeric segment 110, the elastomeric segment 110 becomes squeezed, as it is an elastomeric material such as silicone rubber, TPE, TPU or UHMW PVC, and the lumen of the elastomeric segment 110 therefore becomes smaller. In this way, by narrowing of the lumen, the flow rate of fluid passing through the elastomeric segment 110 and subsequently downstream through an IV tube 24 can be regulated.

Further, due to the reduced compression set performance of the elastomeric segment 110 in comparison to the compression set performance of the IV tube 24, the force of the fluid in the elastomeric segment 110 exerts no biasing force or a minimal biasing force against the flow-regulating member 128. Accordingly, slippage of the flow-regulating member 128 (e.g., the roller wheel 28 rolls back) from the adjusted position does not occur at all or is very slight.

Figure 4:
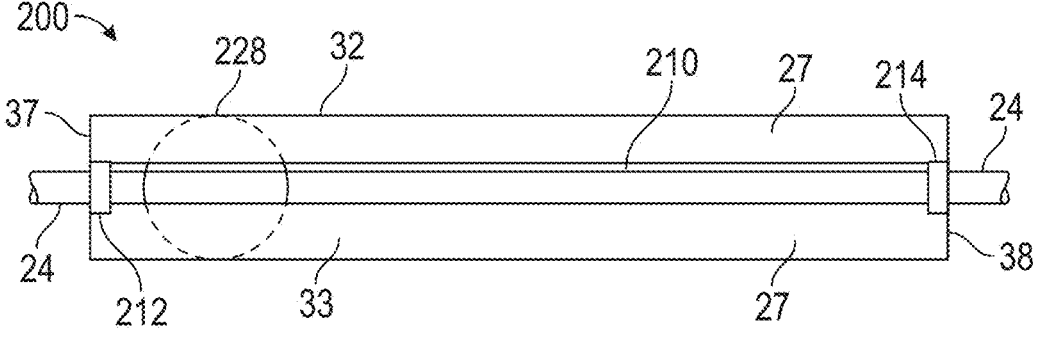
FIG. 4 depicts a top view of a high accuracy clamp assembly with a ball, according to aspects of the disclosure.
Figure 5:
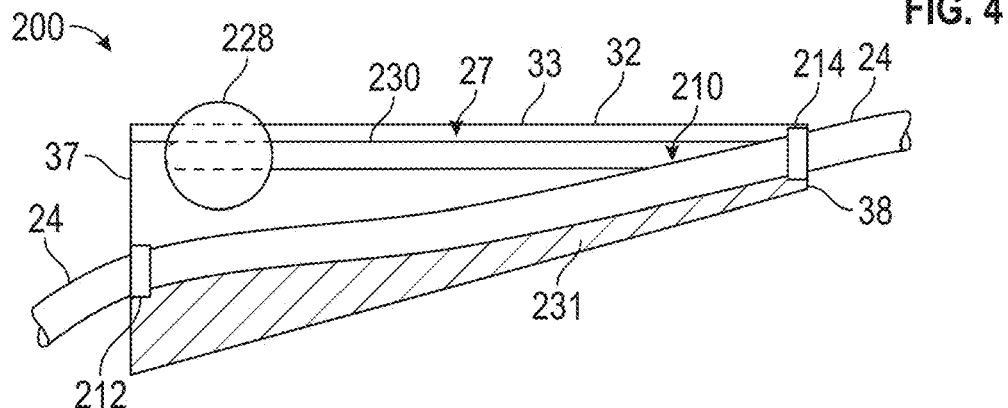
FIG. 5 depicts a cross-section side view of the high accuracy clamp assembly of FIG. 4, according to aspects of the disclosure.
Figure 5A:
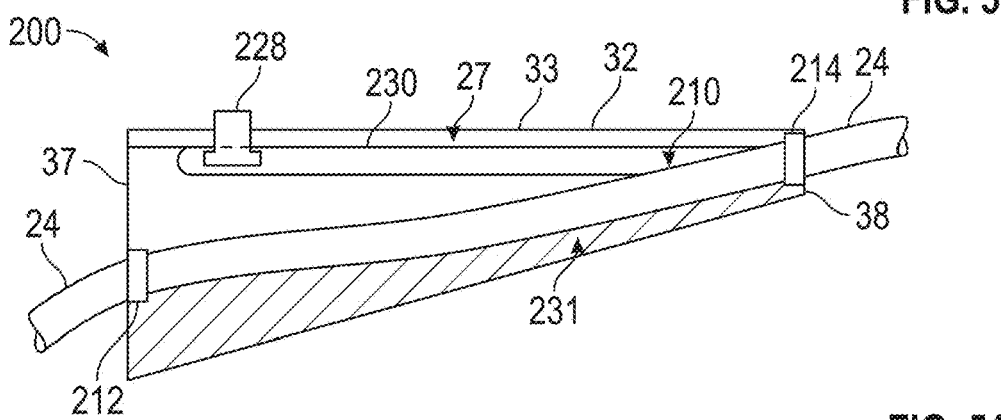
FIG. 5A depicts a cross-section side view of the high accuracy clamp assembly of FIG. 4 with a slider, according to aspects of the disclosure.

As shown in FIGS. 4, 5 and 5A, a high accuracy clamp assembly 200 is shown. The high accuracy clamp assembly 200 may have some of the features of roller clamp 26 or high accuracy clamp assembly 100. For example, high accuracy clamp 200 illustrated in FIGS. 4 and 5 has a housing 32 with two opposing side walls 27 having guide tracks 230 that are aligned with each other and face each other. A flow-regulating member 228 is movably coupled to the guide tracks 230, the flow-regulating member 228 being any of a roller wheel, a ball (e.g., glass ball) and a slider, for example.

For example, the flow-regulating member 228 may be roller wheel 28 having axially-projecting shafts 29 protruding from the centers of each side of the roller wheel 28, where the shafts 29 of the roller 28 are captured by and seated in the guide tracks 230 so that the roller wheel 28 can move up and down the guide tracks 230 along the housing 32, similar to that shown in FIG. 3. Here, a portion of the roller wheel 28 is disposed above a top surface 33 of the housing 32 so that the roller wheel 28 may be manipulated by a user to move the roller wheel 28 along the guide tracks 230.

As another example as shown in FIGS. 4 and 5, the flow-regulating member 228 may be a glass ball and the guide tracks 230 are sized and shaped so that the glass ball can move up and down the guide tracks 230 along the housing 32. Thus, the guide tracks 230 may be concave shaped to closely match the spherical shape of the glass ball so that the glass ball fits snugly within the guide tracks 230. Here, a portion of the glass ball is disposed above the top surface 33 of the housing 32 so that the glass ball may be manipulated by a user to move the glass ball along the guide tracks 230.

In yet another example as shown in FIG. 5A, the flow-regulating member 228 may be a slider and the guide tracks 230 are sized and shaped so that the slider can move up and down the guide tracks 230 along the housing 32. Thus, the guide tracks 230 may be rectangularly shaped to closely match a rectangular shape of the slider so that the slider fits snugly within the guide tracks 230, for example. Here, a protrusion of the slider is disposed above the top surface 33 of the housing 32 so that the slider may be manipulated by a user to move the slider along the guide tracks 230.

Further, instead of receiving standard PVC IV tubing (e.g., IV tube 24) within the housing 32 as is done in roller clamp 26, the high accuracy clamp assembly 200 further includes an elastomeric membrane 210 disposed within the housing 32. The elastomeric membrane 210 is disposed between the two opposing side walls 27, the flow-regulating member 228 and a guide wall 231 that is opposed to the flow-regulating member 228. The elastomeric membrane 210 may be formed of an elastomeric material such as silicone rubber, TPE, TPU or UHMW PVC, for example.

The elastomeric membrane 210 includes a tubing port 212 on the first housing end 37 and a tubing port 214 on the second housing end 38. Here, each of the tubing ports 212, 214 is configured to sealingly couple with an end of an IV tube 24 (e.g., PVC tubing). The elastomeric membrane 210 may be overmolded into the housing 32, such as onto or immediately adjacent the guide wall 231. Thus, the elastomeric membrane 210 is an enclosed or sealed membrane that provides a leak free fluid path between the tubing ports 212, 214.

In use, moving the flow-regulating member 228 downwardly along the guide tracks 230 in the direction of the gradually closer guide wall 231 causes the flow-regulating member 228 to impinge against the elastomeric membrane 210. As the flow-regulating member 228 impinges on the elastomeric membrane 210, the elastomeric membrane 210 becomes squeezed, as it is an elastomeric material such as silicone rubber, TPE, TPU or UHMW PVC, and the lumen of the elastomeric membrane 210 therefore becomes smaller. In this way, by narrowing of the lumen, the flow rate of fluid passing through the elastomeric membrane 210 and subsequently downstream through an IV tube 24 can be regulated.

Further, due to the reduced compression set performance of the elastomeric membrane 210 in comparison to the compression set performance of the IV tube 24, the force of the fluid in the elastomeric membrane 210 exerts no biasing force or a minimal biasing force against the flow-regulating member 228. Accordingly, slippage of the flow-regulating member 228 (e.g., the flow-regulating member 228 moves back) from the adjusted position does not occur at all or is very slight.

Figure 6:
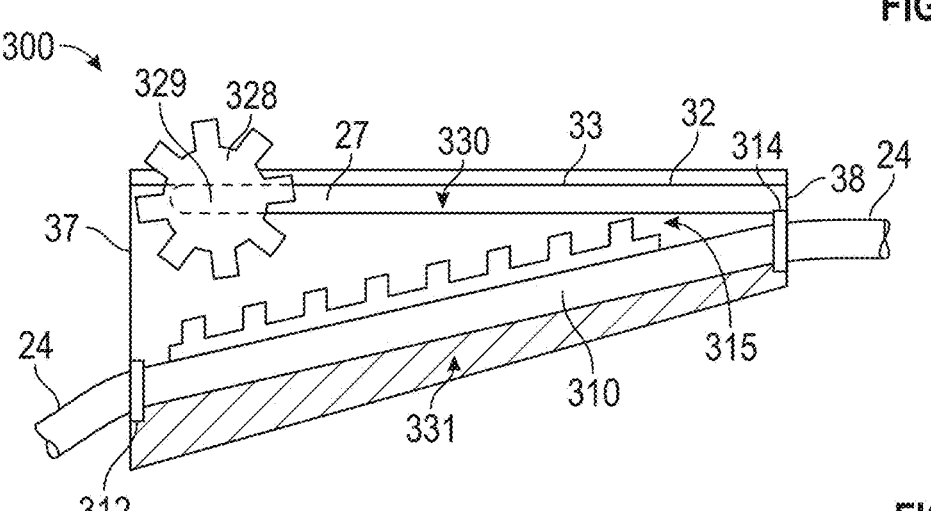
FIG. 6 depicts a cross-section side view of a high accuracy clamp assembly, according to aspects of the disclosure.

As shown in FIG. 6, a high accuracy clamp assembly 300 is shown. The high accuracy clamp assembly 300 may have some of the features of roller clamp 26 or high accuracy clamp assembly 100, 200. For example, high accuracy clamp 300 illustrated in FIG. 6 has a housing 32 with two opposing side walls 27 having guide tracks 330 that are aligned with each other and face each other. A flow-regulating member 328 is movably coupled to the guide tracks 330, the flow-regulating member 328 being a geared slider, for example.

The flow-regulating member 328 may have axially-projecting shafts 329 protruding from the centers of each side of the flow-regulating member 328, where the shafts 329 are captured by and seated in the guide tracks 330 so that the flow-regulating member 328 can move up and down the guide tracks 330 along the housing 32. Here, a portion of the flow-regulating member 328 is disposed above a top surface 33 of the housing 32 so that the flow-regulating member 328 may be manipulated by a user to move the flow-regulating member 328 along the guide tracks 330.

Similarly to high accuracy clamp assembly 200, instead of receiving standard PVC IV tubing (e.g., IV tube 24) within the housing 32 as is done in roller clamp 26, the high accuracy clamp assembly 300 further includes an elastomeric membrane 310 disposed within the housing 32. The elastomeric membrane 310 is disposed between the two opposing side walls 27, the flow-regulating member 328 and a guide wall 331 that is opposed to the flow-regulating member 328.

The elastomeric membrane 310 may be formed of an elastomeric material such as silicone rubber, TPE, TPU or UHMW PVC, for example. The elastomeric membrane 310 includes a tubing port 312 on the first housing end 37 and a tubing port 314 on the second housing end 38, each of the tubing ports 212, 214 configured to sealingly couple with an end of an IV tube 24 (e.g., PVC tubing). The elastomeric membrane 310 may be overmolded into the housing 32, such as onto or immediately adjacent the guide wall 331. Thus, the elastomeric membrane 310 is an enclosed or sealed membrane that provides a leak free fluid path between the tubing ports 312, 314.

The elastomeric membrane 310 further includes gear protrusions 315 disposed on the non-fluid path surface opposing the flow-regulating member 328. The gear protrusions 315 can mesh with the flow-regulating member 328 for finer control and to prevent accidental movement of the flow-regulating member 328.

In use, moving the flow-regulating member 328 downwardly along the guide tracks 330 in the direction of the gradually closer guide wall 331 causes the flow-regulating member 328 to impinge against the elastomeric membrane 310. As the flow-regulating member 328 impinges on the elastomeric membrane 310, the elastomeric membrane 310 becomes squeezed, as it is an elastomeric material such as silicone rubber, TPE, TPU or UHMW PVC, and the lumen of the elastomeric membrane 310 therefore becomes smaller. In this way, by narrowing of the lumen, the flow rate of fluid passing through the elastomeric membrane 310 and subsequently downstream through an IV tube 24 can be regulated.

Further, due to the reduced compression set performance of the elastomeric membrane 310 in comparison to the compression set performance of the IV tube 24, the force of the fluid in the elastomeric membrane 310 exerts no biasing force or a minimal biasing force against the flow-regulating member 328. Accordingly, slippage of the flow-regulating member 328 (e.g., the flow-regulating member 328 moves back) from the adjusted position does not occur at all or is very slight. Also, the meshing of the gear protrusions 315 and the flow-regulating member 328 further function to keep the flow-regulating member 328 in the adjusted position. Further, the meshing of the gear protrusions 315 and the flow-regulating member 328 may require less material in manufacturing to produce a clamp (e.g., high accuracy clamp assembly 300) that stays in place when set by the clinician.

In aspects of the disclosure, the precision roller clamp assembly 100, 200, 300 may be used with any standard IV set, where the housing 32 is disposed between two ends of standard IV tubing (e.g., IV tube 24) and each end is coupled to one of the tubing ports 112, 114, 212, 214, 312, 314.

In aspects of the disclosure, the precision roller clamp assembly 100, 200, 300 may cause complete flow stoppage when the flow-regulating member 128, 228, 328 is positioned at a particular portion (e.g., near the second housing end 38) of the housing 32. For example, the flow-regulating member 128, 228, 328 is able to occlude flow during pressure spikes (e.g., during a syringe push) when the flow-regulating member 128, 228, 328 is so positioned. Further, the position of the flow-regulating member 128, 228, 328 near the second housing end 38 of the housing 32 provides an easy and instant visual notice to a clinician or other user that the flow rate is stopped.

In aspects of the disclosure, the high accuracy clamp assembly 100, 200, 300 provides for flow stability at any given position of the flow-regulating member 128, 228, 328. For example, the elastomeric segment 110, elastomeric membrane 210, 310 is appropriately constrained between the flow-regulating member 128, 228, 328 and the guide wall 31, 231, 331 over a defined movement range of the flow-regulating member 128, 228, 328, so that the compression set performance of the elastomeric segment 110, elastomeric membrane 210, 310 does not cause unintended movement of the flow-regulating member 128, 228, 328.

In aspects of the disclosure, the elastomeric segment 110 and elastomeric membranes 210, 310 have a minimum compression of 10 percent to 15 percent (e.g., 12 percent). In aspects of the disclosure, the elastomeric segment 110 and elastomeric membranes 210, 310 have little or no hysteresis.

Figure 7:
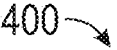
FIG. 7 depicts a method of operating a high accuracy clamp assembly, according to aspects of the disclosure.
Figure 7:
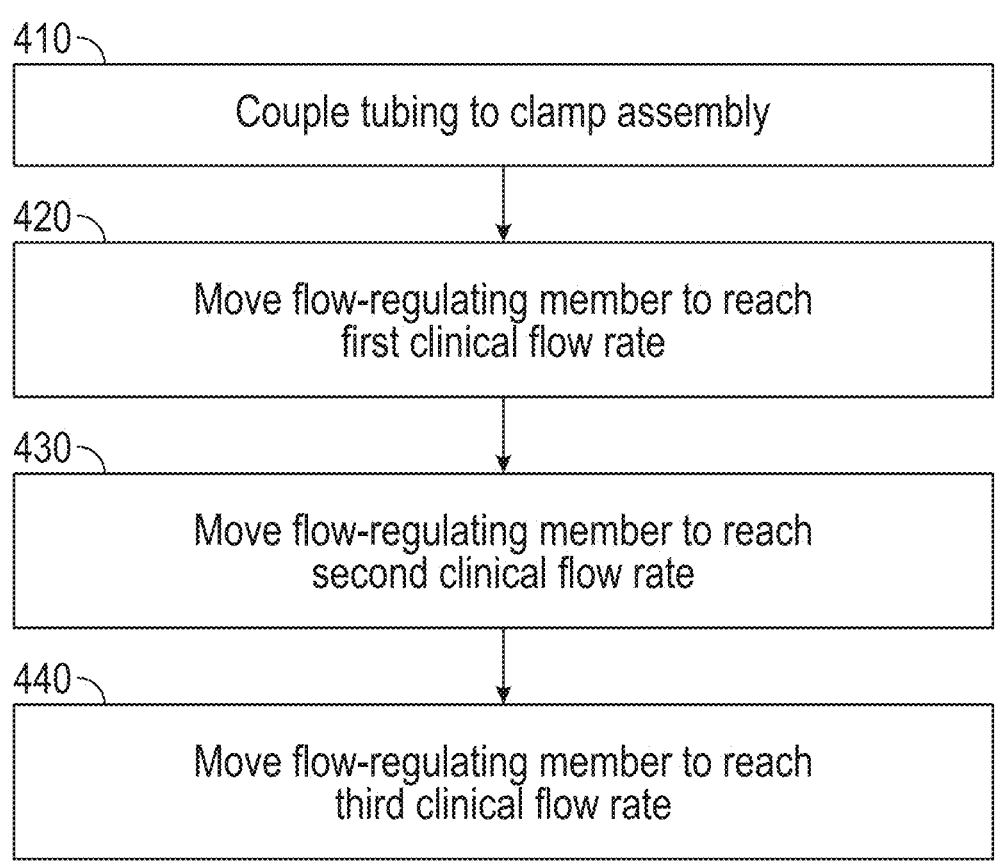

With reference to FIG. 7, a method 400 of operating a high accuracy clamp assembly is provided. In step 410, tubing (e.g., IV tube 24) is coupled to high accuracy clamp assembly 100, 200, 300. For example, a first tube 24 may be inserted into a first tubing port 112, 212, 312 and a second tube 24 may be inserted into a second tubing port 114, 214, 314 with the flow-regulating member 128, 228, 328 in a wide open position closest to the first housing end 37 (e.g., minimally contacting or impinging the elastomeric segment 110, elastomeric membrane 210, 310).

In step 420, the flow-regulating member 128, 228, 328 may be moved through a travel range to engage and impinge the elastomeric segment 110, elastomeric membrane 210, 310. For example, the flow-regulating member 128, 228, 328 may be moved from the first housing end 37 of the housing 32 towards the second housing end 38 of the housing 32, so that a narrowing between the guide wall 31, 231, 331 and the elastomeric segment 110, elastomeric membrane 210, 310 causes the flow-regulating member 128, 228, 328 to compress or squeeze the contacted portion of the elastomeric segment 110, elastomeric membrane 210, 310. This compression causes the fluid flow rate in the elastomeric segment 110, elastomeric membrane 210, 310 to change from a full open flow rate to a first controlled clinical flow rate (e.g., from full open to 250 ml/hr.

In step 430, the flow-regulating member 128, 228, 328 may be moved to another portion of the travel range of the flow-regulating member 128, 228, 328 to further impinge the elastomeric segment 110, elastomeric membrane 210, 310. For example, the flow-regulating member 128, 228, 328 may be moved so that a further narrowing between the guide wall 31, 231, 331 and the elastomeric segment 110, elastomeric membrane 210, 310 causes the flow-regulating member 128, 228, 328 to further compress or squeeze the contacted portion of the elastomeric segment 110, elastomeric membrane 210, 310, thus causing the fluid flow rate in the elastomeric segment 110, elastomeric membrane 210, 310 to change from the first controlled clinical flow rate to a second controlled clinical flow rate (e.g., from 250 ml/hr to 25 ml/hr).

In step 440, the flow-regulating member 128, 228, 328 may be moved to another portion of the travel range of the flow-regulating member 128, 228, 328 to further impinge the elastomeric segment 110, elastomeric membrane 210, 310. For example, the flow-regulating member 128, 228, 328 may be moved so that a further narrowing between the guide wall 31, 231, 331 and the elastomeric segment 110, elastomeric membrane 210, 310 causes the flow-regulating member 128, 228, 328 to even further compress or squeeze the contacted portion of the elastomeric segment 110, elastomeric membrane 210, 310, thus causing the fluid flow rate in the elastomeric segment 110, elastomeric membrane 210, 310 to change from the second controlled clinical flow rate to a third controlled clinical flow rate (e.g., from 25 ml/hr to 0 ml/hr).

In one or more embodiments of the disclosure, a clamp assembly comprises: a housing configured to couple to an infusion set, the housing comprising: two opposing side walls spaced apart from each other, each side wall having an opposing guide groove longitudinally positioned in an interior surface; a guide wall disposed between the side walls; an elastomeric segment disposed between the two opposing side walls and the guide wall, the elastomeric segment having a lower compression set performance that the compression set performance of first and second IV tubes of the infusion set; a first tubing port disposed on a first end of the elastomeric segment and configured to couple with the first IV tube of the infusion set; and a second tubing port disposed on a second end of the elastomeric segment and configured to couple with the second IV tube of the infusion set; and a roller wheel having two axial projections slidingly seated in the guide grooves, the roller configured to move along a longitudinal axis of the housing over a movement range as the projections slide in the guide grooves, wherein the roller wheel is configured to remain in a set position during use of the infusion set based on the compression set performance of the elastomeric segment until the roller wheel is moved by a user.

In aspects of the disclosure, the elastomeric segment is disposed between the guide wall and the roller wheel. In aspects of the disclosure, the elastomeric segment is formed from silicone rubber. In aspects of the disclosure, the elastomeric segment is formed from Thermoplastic Polyurethane (TPU). In aspects of the disclosure, the elastomeric segment is formed from Thermoplastic Elastomer (TPE). In aspects of the disclosure, the elastomeric segment is formed from ultra-high molecular weight Polyvinyl Chloride (UHMW PVC). In aspects of the disclosure, the first and second IV tubes of the infusion set are formed from Polyvinyl Chloride (PVC).

In one or more embodiments of the disclosure, a clamp assembly comprises: a housing configured to couple to an infusion set, the housing comprising: two opposing side walls spaced apart from each other, each side wall having an opposing guide track longitudinally positioned in an interior surface; a guide wall disposed between the side walls; an elastomeric membrane disposed on the guide wall between the two opposing side walls, the elastomeric membrane having a lower compression set performance that the compression set performance of first and second intravenous (IV) tubes of the infusion set; a first tubing port disposed on a first end of the elastomeric membrane and configured to couple with the first IV tube of the infusion set; and a second tubing port disposed on a second end of the elastomeric membrane and configured to couple with the second IV tube of the infusion set; and a flow-regulating member having two portions slidingly seated in the guide tracks, the flow-regulating member configured to move along a longitudinal axis of the housing over a movement range as the two portions slide in the guide tracks, wherein the flow-regulating member is configured to remain in a set position during use of the infusion set based on the compression set performance of the elastomeric membrane until the flow-regulating member is moved by a user.

In aspects of the disclosure, the elastomeric membrane is disposed between the guide wall and the flow-regulating member. In aspects of the disclosure, the elastomeric membrane is formed from silicone rubber. In aspects of the disclosure, the elastomeric membrane is formed from Thermoplastic Polyurethane (TPU). In aspects of the disclosure, the elastomeric membrane is formed from Thermoplastic Elastomer (TPE). In aspects of the disclosure, the first and second IV tubes of the infusion set are formed from Polyvinyl Chloride (PVC).

In aspects of the disclosure, the flow-regulating member comprises a roller wheel having two axial projections slidingly seated in the guide tracks, and wherein a portion of the roller wheel extends above a top surface of the housing. In aspects of the disclosure, the flow-regulating member comprises a ball having two curved portions slidingly seated in the correspondingly curved guide tracks, and wherein a portion of the ball extends above a top surface of the housing. In aspects of the disclosure, the flow-regulating member comprises a slider having two portions slidingly seated in the correspondingly shaped guide tracks, and wherein a protrusion of the slider extends above a top surface of the housing. In aspects of the disclosure, the elastomeric membrane is overmolded into the housing and comprises an enclosed fluid pathway between the first and second tubing ports.

In aspects of the disclosure, the flow-regulating member comprises a geared slider having two axial projections slidingly seated in the guide tracks, and wherein a portion of the geared slider extends above a top surface of the housing. In aspects of the disclosure, the elastomeric membrane is overmolded into the housing and comprises an enclosed fluid pathway between the first and second tubing ports, and wherein the elastomeric membrane comprises gear protrusions disposed on a non-fluid path surface opposing the geared slider, the gear protrusions configured to mesh with the geared slider. In aspects of the disclosure, the elastomeric membrane has a minimum compression of 10 percent to 15 percent.

In one or more embodiments of the disclosure, a method of operating a clamp assembly comprises inserting a first intravenous (IV) tube of an infusion set into a first tubing port of a high accuracy clamp assembly; inserting a second IV tube of the infusion set into a second tubing port of the high accuracy clamp assembly, the high accuracy clamp assembly comprising a housing having two opposing side walls spaced apart from each other, each side wall having an opposing guide groove longitudinally positioned in an interior surface, a guide wall disposed between the side walls, an elastomeric membrane disposed on the guide wall between the two opposing side walls and between the first and second tubing ports, and a flow-regulating member slidingly seated in the guide grooves; moving the flow-regulating member to a first position along the guide groove to engage the elastomeric membrane, causing a flow rate of fluid through the elastomeric membrane to go from a fully open flow rate to a first controlled clinical flow rate; and maintaining the flow-regulating member in the first position during use of the infusion set until the flow-regulating member is moved again by a user based on a compression set performance of the elastomeric membrane being lower than the compression set performance of the first and second IV tubes of the infusion set.

It is understood that any specific order or hierarchy of blocks in the methods of processes disclosed is an illustration of example approaches. Based upon design or implementation preferences, it is understood that the specific order or hierarchy of blocks in the processes may be rearranged, or that all illustrated blocks be performed. In some implementations, any of the blocks may be performed simultaneously.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

As used herein, the phrase "at least one of" preceding a series of items, with the term "or" to separate any of the items, modifies the list as a whole, rather than each item of the list. The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, or C" may refer to: only A, only B, or only C; or any combination of A, B, and C.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that the specific order or hierarchy of steps, operations or processes disclosed is an illustration of exemplary approaches. Based upon design preferences, it is understood that the specific order or hierarchy of steps, operations or processes may be rearranged. Some of the steps, operations or processes may be performed simultaneously. Some or all of the steps, operations, or processes may be performed automatically, without the intervention of a user. The accompanying method claims, if any, present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112 (f) unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but are to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A clamp assembly comprising:
   a housing configured to couple to an infusion set, the housing comprising:
      two opposing side walls spaced apart from each other, each side wall having an opposing guide track longitudinally positioned in an interior surface;
      a guide wall disposed between the side walls;
      an elastomeric membrane disposed on the guide wall between the two opposing side walls, the elastomeric membrane having a lower compression set performance that the compression set performance of first and second intravenous (IV) tubes of the infusion set;
      a first tubing port disposed on a first end of the elastomeric membrane and configured to couple with the first IV tube of the infusion set; and
      a second tubing port disposed on a second end of the elastomeric membrane and configured to couple with the second IV tube of the infusion set; and
   a flow-regulating member having two portions slidingly seated in the guide tracks, the flow-regulating member configured to move along a longitudinal axis of the housing over a movement range as the two portions slide in the guide tracks,
   wherein the flow-regulating member is configured to remain in a set position during use of the infusion set based on the compression set performance of the elastomeric membrane until the flow-regulating member is moved by a user,
   wherein the flow-regulating member comprises a geared slider having two axial projections slidingly seated in the guide tracks, and wherein a portion of the geared slider extends above a top surface of the housing,
   wherein the elastomeric membrane is overmolded into the housing and comprises an enclosed fluid pathway between the first and second tubing ports, and
   wherein the elastomeric membrane comprises gear protrusions disposed on a non-fluid path surface opposing the geared slider, the gear protrusions configured to mesh with the geared slider.

2. The clamp assembly of claim 1, wherein the elastomeric membrane is disposed between the guide wall and the flow-regulating member.

3. The clamp assembly of claim 1, wherein the elastomeric membrane is formed from silicone rubber.

4. The clamp assembly of claim 1, wherein the elastomeric membrane is formed from one Thermoplastic Polyurethane (TPU) and Thermoplastic Elastomer (TPE).

5. The clamp assembly of claim 1, wherein the elastomeric membrane is formed from ultra-high molecular weight Polyvinyl Chloride (UHMW PVC).

6. The clamp assembly of claim 1, wherein the first and second IV tubes of the infusion set are formed from Polyvinyl Chloride (PVC).

7. The clamp assembly of claim 1, wherein the elastomeric membrane has a minimum compression of 10 percent to 15 percent.

8. A method of operating the clamp assembly of claim 1, the method comprising:
   inserting the first IV tube of the infusion set into the first tubing port of the clamp assembly;
   inserting the second IV tube of the infusion set into the second tubing port of the clamp assembly;
   moving the flow-regulating member to a first position along the guide tracks to engage the elastomeric membrane, causing a flow rate of fluid through the elastomeric membrane to go from a fully open flow rate to a first controlled clinical flow rate; and
   maintaining the flow-regulating member in the first position during use of the infusion set until the flow-regulating member is moved again by a user based on the compression set performance of the elastomeric membrane being lower than the compression set performance of the first and second IV tubes of the infusion set.

* * * * *